(12) United States Patent
Kather et al.

(10) Patent No.: US 6,756,342 B1
(45) Date of Patent: Jun. 29, 2004

(54) SUBSTITUTED THIENOCYCLOALK(EN)YLAMINO -1,3,5-TRIAZINE

(75) Inventors: Kristian Kather, Köln (DE); Stefan Lehr, Langenfeld (DE); Hans-Jochem Riebel, Selters (DE); Katharina Voigt, Monheim (DE); Mark Wilhelm Drewes, Langenfeld (DE); Dieter Feucht, Monheim (DE); Rolf Pontzen, Leichlingen (DE); Ingo Wetcholowsky, Cond. Estancia Marambaia (BR)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/031,645

(22) PCT Filed: May 2, 2000

(86) PCT No.: PCT/EP00/03928

§ 371 (c)(1),
(2), (4) Date: Mar. 4, 2002

(87) PCT Pub. No.: WO00/69854

PCT Pub. Date: Nov. 23, 2000

(30) Foreign Application Priority Data

May 12, 1999 (DE) .......................................... 199 21 883

(51) Int. Cl.⁷ .................... C07D 495/02; C07D 409/12; C07D 333/50; A01N 43/68
(52) U.S. Cl. ...................... 504/230; 544/207; 544/212; 549/49; 549/50
(58) Field of Search ............................... 544/207, 212; 504/230

(56) References Cited

U.S. PATENT DOCUMENTS

| | | | |
|---|---|---|---|
| 3,301,874 A | 1/1967 | Sam .................... | 260/332.3 |
| 4,740,230 A | 4/1988 | Takematsu et al. ........... | 71/90 |
| 6,284,710 B1 | 9/2001 | Riebel et al. ................ | 504/234 |
| 6,346,503 B1 | 2/2002 | Riebel et al. ................ | 504/234 |
| 6,348,435 B1 | 2/2002 | Riebel et al. ................ | 504/230 |
| 6,403,794 B2 | 6/2002 | Riebel et al. ................ | 544/242 |
| 2002/0016459 A1 | 2/2002 | Riebel et al. ................ | 544/206 |

FOREIGN PATENT DOCUMENTS

| | | |
|---|---|---|
| DE | 197 44 232 | 4/1999 |
| EP | 0 283 522 | 9/1988 |

OTHER PUBLICATIONS

J. Pharm. Sci., 52, (month unavailable) 1963, pp. 898–901, Thiaindanones Thiophene Isosteres of Indanone by J. Sam and A. C. Thompson.
J. Org. Chem., 18, (month unavailable) 1953, pp. 1511–1515, Synthesis of 4–Substituted Thianaphthene Derivatives by M. C. Kloetzel, J. E. Little, Jr. and D. M. Frisch.
J. Chem Soc., (month unavailable) 1953, pp. 1837–1842, The Orientation of Substitution in the Isomeric Thiophthens. The Synthesis of Solid Thiophthen [Thiopheno(3' : 2'-2 : 3)thiophen]. by F. Challenger and J. L. Holmes.
Heterocycl. Chem., 2, (month unavailable) 1965, pp. 44–48, A Synthesis of 7 Substituted Benzo[b]thiophene Derivatives by d. W. H. MacDowell and T. D. Greenwood.
Heterocycl. Chem., 29, Aug.–Sep. 1992, pp. 1213–1217, Studies in Sulphur Heterocycles. Part 7 [1] Tricyclic Compounds Related to 5,6,7,8–Tetrahydro–4H–cyclohepta[b]thiophene by A. De, S. Bhattacharay (nee Mazumder [2], S. S. Jash, S. Mukherjee, U. Saha and P. K. Sen.
Heterocycl. Chem., 17, (month unavailable) 1980, pp. 87–92, Studies on Sulphur Heterocycles.Reactions of 6,7–Dihydrobenzo[b]thiophen–4(5H)one Derivatives and their Conversion to 7– Substituted Thienol[2,3–h][1]benzopyran–8–ones by C. M. Asprou, J. S. A. Brunskill, H. Jeffrey and A. De.

*Primary Examiner*—Venkataraman Balasubramanian
(74) *Attorney, Agent, or Firm*—Richard E. L. Henderson; Raymond J. Harmuth

(57) ABSTRACT

The invention relates to novel substituted thienocycloalk(en)ylamino-1,3,5-triazines of the general formula (I)

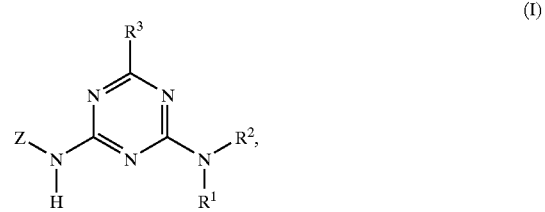

in which Z, $R^1$, $R^2$, $R^3$ are as defined in the description, and to processes for their preparation, to there use as herbicides and to the intermediates required for their preparation including their preparation processes in the case of the preferred compounds.

10 Claims, No Drawings

SUBSTITUTED THIENOCYCLOALK(EN)YLAMINO -1,3,5-TRIAZINE

The invention relates to novel substituted thienocycloalk(en)ylamino-1,3,5-triazines, to processes for their preparation including the novel intermediates, and to their use as herbicides.

A number of substituted thienylalkylamino-1,3,5-triazines are already known from the (patent) literature (cf. WO-A-98/15537, WO-A-98/15539, DE-A-19744232). However, these compounds have hitherto not attained any particular importance. Substituted thienocycloalk(en)ylamino-1,3,5-triazines have hitherto not been disclosed at all.

This invention, accordingly, provides the novel thienocycloalk(en)ylamino-1,3,5-triazines of the general formula (I)

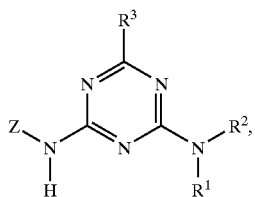

(I)

in which $R^1$ represents hydrogen or represents optionally substituted alkyl, $R^2$ represents hydrogen, represents formyl or represents in each case optionally substituted alkyl, alkylcarbonyl, alkoxycarbonyl or alkylaminocarbonyl, or the grouping $N(R^1R^2)$ also represents dialkylaminoalkylideneamino, $R^3$ represents hydrogen, represents halogen, represents optionally substituted alkyl, represents in each case optionally substituted alkylcarbonyl, alkoxycarbonyl, alkoxy, alkylthio, alkylsulphinyl or alkylsulphonyl, represents in each case optionally substituted alkenyl or alkinyl, or represents optionally substituted cycloalkyl, and Z represents one of the thienocycloalk(en)yl groupings below

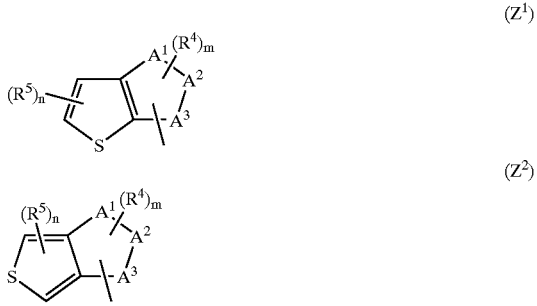

in which m represents the numbers 0, 1, 2, 3 or 4, n represents the numbers 0, 1 or 2, $A^1$ represents O (oxygen), S (sulphur), —CO—, —CS— or alkanediyl (alkylene), $A^2$ represents O (oxygen), S (sulphur), —CO—, —CS— or alkanediyl (alkylene), $A^3$ represents O (oxygen), S (sulphur), —CO—, —CS— or alkanediyl (alkylene), with the proviso that at least one of the groupings $A^1$, $A^2$, $A^3$ represents alkanediyl and that two adjacent groups do not simultaneously represent S or O—

$R^4$ represents amino, cyano, carbamoyl, thiocarbamoyl, formyl, halogen, or represents in each case optionally substituted alkyl, alkylcarbonyl, alkoxy, alkoxycarbonyl, alkylthio, alkylsulphinyl, alkylsulphonyl, alkylamino, dialkylamino, alkylcarbonylamino, alkoxycarbonylamino, alkylsulphonylamino, alkenyl, alkinyl, alkenylcarbonyl, alkinylcarbonyl, carbonyl, aryl arylcarbonyl or arylalkyl, and $R^5$ represents nitro, amino, cyano, carbamoyl, thiocarbamoyl, formyl, halogen, or represents in each case optionally substituted alkyl, alkylcarbonyl, alkoxy, alkoxycarbonyl, alkylthio, alkylsulphinyl, alkylsulphonyl, alkylamino, dialkylamino, alkylcarbonylamino, alkoxycarbonylamino, alkylsulphonylamino, alkenyl, alkinyl, alkenylcarbonyl, alkinylcarbonyl, aryl, arylcarbonyl or arylalkyl.

Saturated or unsaturated hydrocarbon groupings, such as alkyl, alkanediyl, alkenyl or alkinyl, are—including in combinations with heteroatoms, such as in alkoxy—in each case straight-chain or branched, as far as this is possible.

Optionally substituted radicals can be mono- or polysubstituted, where in the case of polysubstitution the substituents can be identical or different.

Preferred substituents or ranges of the radicals present in the formulae shown above and below are defined below.

m preferably represents the numbers 0, 1 or 2.

$A^1$ preferably represents O (oxygen), S (sulphur), —CO—, —CS— or alkanediyl (alkylene) having 1 to 3 carbon atoms.

$A^2$ preferably represents O (oxygen), S (sulphur), —CO—, —CS— or alkanediyl (alkylene) having 1 to 3 carbon atoms.

$A^3$ preferably represents O (oxygen), S (sulphur), —CO—, —CS— or alkanediyl (alkylene) having 1 to 3 carbon atoms.

In the preferred compounds, at least one of the groupings $A^1$, $A^2$, $A^3$ represents alkanediyl having 1 to 3 carbon atoms, and two adjacent groups do not simultaneously represent S or O.

$R^1$ preferably represents hydrogen or represents optionally cyano-, halogen- or $C_1$–$C_4$-alkoxy-substituted alkyl having 1 to 6 carbon atoms.

$R^2$ preferably represents hydrogen, represents formyl or represents in each case optionally cyano-, halogen- or $C_1$–$C_4$-alkoxy-substituted alkyl, alkylcarbonyl, alkoxycarbonyl or alkylaminocarbonyl having in each case 1 to 6 carbon atoms in the alkyl groups.

The grouping $N(R^1R^2)$ preferably also represents dialkylaminoalkylideneamino having in each case up to 4 carbon atoms in the alkyl groups or alkylidene groups.

$R^3$ preferably represents hydrogen, represents halogen, represents optionally cyano-, halogen-, hydroxyl-, $C_1$–$C_4$-alkoxy- or $C_1$–$C_4$-alkylthio-substituted alkyl having 1 to 6 carbon atoms, represents in each case optionally cyano-, halogen- or $C_1$–$C_4$-alkoxy-substituted alkylcarbonyl, alkoxycarbonyl, alkoxy, alkylthio, alkylsulphinyl or alkylsulphonyl having in each case 1 to 6 carbon atoms in the alkyl groups, represents in each case optionally halogen-substituted alkenyl or alkinyl having in each case 2 to 6 carbon atoms, or represents optionally cyano-, halogen- or $C_1$–$C_4$-alkyl-substituted cycloalkyl having 3 to 6 carbon atoms.

$R^4$ preferably represents amino, cyano, carbamoyl, thiocarbamoyl, formyl, halogen, represents in each case optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, dialkylamino, alkylcarbonylamino, alkoxycarbonylamino or alkylsulphonylamino having in each case 1 to 6 carbon atoms in the alkyl groups, represents in each case optionally cyano- or halogen-substituted alkenyl, alkinyl, alkenylcarbonyl or alkinylcarbonyl having in each case 2 to 6 carbon atoms in the alkenyl or alkinyl groups, or represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy- or $C_1$–$C_4$-alkoxy-carbonyl-substituted aryl, arylcarbonyl or arylalkyl having in each case 6 or 10 carbon atoms in the aryl group and optionally 1 to 4 carbon atoms in the alkyl moiety.

$R^5$ preferably represents nitro, amino, cyano, carbamoyl, thiocarbamoyl, formyl, halogen, represents in each case optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, dialkylamino, alkylcarbonylamino, alkoxycarbonylamino or alkylsulphonylamino having in each case 1 to 6 carbon atoms in the alkyl groups, represents in each case optionally cyano- or halogen-substituted alkenyl, alkinyl, alkenylcarbonyl or alkinylcarbonyl having in each case 2 to 6 carbon atoms in the alkenyl or alkinyl groups, or represents in each case optionally nitro-, cyano:-, halogen-, $C_1$–$C_4$-alkyl-, $C_1$–$C_4$-halogenoalkyl-, $C_1$–$C_4$-alkoxy-, $C_1$–$C_4$-halogenoalkoxy- or $C_1$–$C_4$-alkoxy-carbonyl substituted aryl, arylcarbonyl or arylalkyl having in each case 6 or 10 carbon atoms in the aryl group and optionally 1 to 4 carbon atoms in the alkyl moiety.

$A^1$ particularly preferably represents O (oxygen), S (sulphur), —CO—, —CS—, methylene, dimethylene or trimethylene.

$A^2$ particularly preferably represents O (oxygen), S (sulphur), —CO—, —CS—, methylene, dimethylene or trimethylene.

$A^3$ particularly preferably represents O (oxygen), S (sulphur), —CO—, —CS—, methylene, dimethylene or trimethylene.

In the preferred compounds, at least one of the groupings $A^1$, $A^2$, $A^3$ represents methylene, dimethylene or trimethylene, and two adjacent groups do not simultaneously represent S or O.

$R^1$ particularly preferably represents hydrogen or represents in each case optionally cyano-, fluorine-, chlorine-, methoxy- or ethoxy-substituted methyl, ethyl, n- or i-propyl.

$R^2$ particularly preferably represents hydrogen, represents formyl or represents in each case optionally cyano-, fluorine-, chlorine-, methoxy- or ethoxy-substituted methyl, ethyl, n- or i-propyl, acetyl, propionyl, n- or i-butyroyl, methoxycarbonyl, ethoxycarbonyl, n- or i-propoxycarbonyl, methylamino-carbonyl, ethylaminocarbonyl, n- or i-propylaminocarbonyl.

The grouping $N(R^1R^2)$ particularly preferably also represents dimethylaminomethyleneamino or diethylaminomethyleneamino.

$R^3$ particularly preferably represents hydrogen, represents fluorine, chlorine, bromine, represents in each case optionally cyano-, fluorine-, chlorine-, bromine-, hydroxyl-, methoxy-, ethoxy-, n- or i-propoxy-, methylthio-, ethylthio-, n- or i-propylthio-substituted methyl, ethyl, n- or i-propyl, n-, i- or s-butyl, represents in each case optionally cyano-, fluorine-, chlorine-, methoxy- or ethoxy- substituted acetyl, propionyl, n- or i-butyroyl, methoxy-carbonyl, ethoxycarbonyl, n- or i-propoxycarbonyl, methoxy, ethoxy, n- or i-propoxy, methylthio, ethylthio, n- or i-propylthio, methylsulphinyl, ethyl-sulphinyl, n- or i-propylsulphinyl, methylsulphonyl, ethylsulphonyl, n- or i-propylsulphonyl, represents in each case optionally fluorine-, chlorine- or bromine-substituted ethenyl, propenyl, butenyl, ethinyl, propinyl or butinyl, or represents in each case optionally cyano-, fluorine-, chlorine-, methyl- or ethyl-substituted cyclopropyl, cyclobutyl, cyclopentyl or cyclohexyl.

$R^4$ particularly preferably represents amino, cyano, carbamoyl, thiocarbamoyl, formyl, fluorine, chlorine, bromine, represents in each case optionally cyano-, fluorine-, chlorine-, methoxy- or ethoxy-substituted methyl, ethyl, n- or i-propyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, n- or i-propyl-sulphinyl, methylsulphonyl, ethylsulphonyl, n- or i-propylsulphonyl, methylamino, ethylamino, n- or i-propylamino, dimethylamino, diethylamino, acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, represents in each case optionally cyano-, fluorine-, chlorine- or bromine-substituted ethenyl, propenyl, butenyl, ethinyl, propinyl, butinyl, ethenylcarbonyl, propenylcarbonyl, butenylcarbonyl, ethinylcarbonyl, propinylcarbonyl or butinyl-carbonyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, tri-fluoromethoxy-, methoxycarbonyl-, ethoxycarbonyl-, n- or i-propoxy-carbonyl-substituted phenyl, benzoyl or benzyl.

$R^5$ particularly preferably represents nitro, amino, cyano, carbamoyl, thio-carbamoyl, formyl, fluorine, chlorine, bromine, represents in each case optionally cyano-, fluorine-, chlorine-, methoxy- or ethoxy-substituted methyl, ethyl, n- or i-propyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethyl-sulphinyl, n- or i-propylsulphinyl, methylsulphonyl, ethylsulphonyl, n- or i-propylsulphonyl, methylamino, ethylamino, n- or i-propylamino, dimethyl-amino, diethylamino, acetylamino, propionylamino, n- or i-butyroylamino, methoxycarbonylamino, ethoxycarbonylamino) n- or i-propoxycarbonylamino, methylsulphonylamino, ethylsulphonylamino, n- or i-propyl-sulphonylamino, represents in each case optionally cyano-, fluorine-, chlorine- or bromine-substituted ethenyl, propenyl, butenyl, ethinyl, propinyl, butinyl, ethenylcarbonyl, propenylcarbonyl, butenylcarbonyl, ethinyl-carbonyl, propinylcarbonyl or butinylcarbonyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxy-carbonyl-, n- or i-propoxycarbonyl-substituted phenyl, benzoyl or benzyl.

$A^1$ very particularly preferably represents methylene or dimethylene.

$A^2$ very particularly preferably represents methylene or dimethylene.

$A^3$ very particularly preferably represents methylene or dimethylene.

$R^2$ very particularly preferably represents hydrogen.

$R^2$ very particularly preferably represents hydrogen, represents formyl or represents in each case optionally fluorine-, chlorine-, methoxy- or ethoxy-substituted acetyl, propionyl, n- or i-butyroyl, methoxycarbonyl, ethoxy-carbonyl, n- or i-propoxycarbonyl.

The grouping $N(R^1R^2)$ very particularly preferably also represents dimethylaminomethyleneamino.

$R^3$ very particularly preferably represents in each case optionally fluorine- or chlorine-substituted methyl, ethyl, n- or i-propyl.

$R^4$ very particularly preferably represents cyano, fluorine, chlorine, bromine, or represents in each case optionally fluorine- or chlorine-substituted methyl, ethyl, methoxy or ethoxy.

$R^5$ very particularly preferably represents nitro, cyano, fluorine, chlorine, bromine, or represents in each case optionally fluorine- or chlorine-substituted methyl, ethyl, methoxy or ethoxy.

In the general formula (I), Z most preferably represents

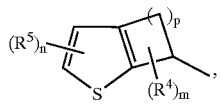

where p represents 2, 3 or 4 and n, m, $R^4$ and $R^5$ are as defined above.

The abovementioned general or preferred radical definitions apply both to the end products of the formula (I) and, correspondingly, to the starting materials or intermediates required in each case for the preparation. These radical definitions can be combined with one another as desired, i.e. including combinations between the given preferred ranges.

Preference according to the invention is given to those compounds of the formula (I) which contain a combination of the meanings given above as being preferred.

Particular preference according to the invention is given to those compounds of the formula (I) which contain a combination of the meanings given above as being particularly preferred.

Very particular preference according to the invention is given to those compounds of the formula (I) which contain a combination of the meaning given above as being very particularly preferred.

Most preference according to the invention is given to those compounds of the formula (I) in which Z has the meaning given as being most preferred.

Saturated or unsaturated hydrocarbon radicals, such as alkyl, alkanediyl or alkenyl, ilk are—including in combination with heteroatoms, such as in alkoxy—in each case straight-chain or branched, as far as this is possible.

Optionally substituted radicals can be mono- or polysubstituted, where in the case of polysubstitution the substituents can be identical or different.

If appropriate, the compounds of the general formula (I) according to the invention contain an asymmetrically substituted carbon atom, in which case they can be present in different enantiomeric (R- and S-configured forms) or diastereomeric forms. The invention relates both to the various possible individual enantiomeric or stereoisomeric forms of the compounds of the general formula (I), and to the mixtures of these isomeric compounds.

The novel substituted thienocycloalk(en)ylamino-1,3,5-triazines of the general formula (I) have interesting biological properties. In particular, they have strong herbicidal activity.

The novel substituted thienocycloalk(en)ylamino-1,3,5-triazines of the general formula (I) are obtained when biguanides of the general formula (II)

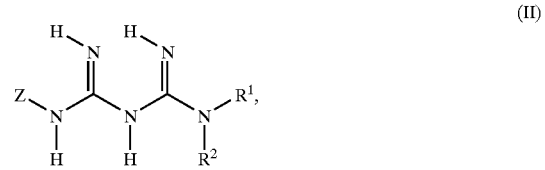

in which $R^1$, $R^2$ and Z are as defined above, and/or acid adducts of compounds of the general formula (II)

are reacted with alkoxycarbonyl compounds of the general formula (III)

in which $R^3$ is as defined above and

R' represents alkyl, if appropriate in the presence of a reaction auxiliary and if appropriate in the presence of a diluent and, if appropriate, further conversions within the scope of the definition of the substituents are carried out by customary methods on the resulting compounds of the general formula (I).

The compounds of the general formula (I) can be converted by customary methods into other compounds of the general formula (I) in accordance with the above definition of the substituents, for example by reacting compounds of the formula (I) in which $R^2$ represents hydrogen with acylating agents, such as, for example, acetyl chloride, acetic anhydride, propionyl chloride, propionic anhydride, methyl chloroformate or ethyl chloroformate (in the case of $R^2$ for example introduction of $COCH_3$, $COC_2H_5$, $COOCH_3$, $COOC_2H_5$ groups for a hydrogen atom).

Using, for example, 1-(4,5,6,7-tetrahydro-benzo[b]thiophen-4-yl)-biguanide and methyl trifluoroacetate as starting materials, the course of the reaction in the process according to the invention can be illustrated by the following formula scheme:

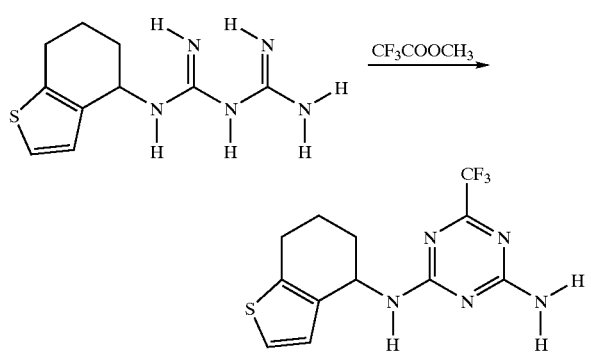

The formula (II) provides a general definition of the biguanides to be used as starting materials in the process according to the invention for preparing compounds of the general formula (I). In the general formula (II), $R^1$, $R^2$ and Z preferably or in particular have those meanings which have already been mentioned above, in connection with the description of the compounds of the general formula (I) according to the invention, as being preferred or as being particularly preferred for $R^1$, $R^2$ and Z.

Suitable acid adducts of compounds of the formula (II) are their adducts with protic acids, such as, for example, with hydrogen chloride, hydrogen bromide, sulphuric acid, methanesulphonic acid, benzenesulphonic acid and p-toluenesulphonic acid.

The starting materials of the general formula (II) have hitherto not been disclosed in the literature; as novel substances, they also form part of the subject-matter of the present application.

The novel biguanides of the general formula (II) are obtained when amino compounds of the general formula (IV)

$$Z-NH_2 \quad (IV)$$

in which

Z is as defined above,
and/or acid adducts of compounds of the general formula (IV), such as, for example, the hydrochlorides
are reacted with cyanoguanidine ("dicyanodiamide") of the formula (V)

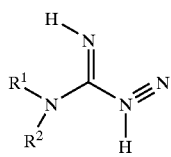

if appropriate in the presence of a reaction auxiliary, such as, for example, hydrogen chloride, and if appropriate in the presence of a diluent, such as, for example, n-decane or 1,2-dichloro-benzene, at temperatures between 100° C. and 200° C. (cf. the Preparation Examples).

The biguanides of the general formula (II) can, after their preparation, also be employed directly, without intermediate isolation, for preparing the compounds of the general formula (I) by the process according to the invention (cf. the Preparation Examples).

The amino compounds of the general formula (IV) required as precursors are known and/or can be prepared by processes known per se (cf. J. Org. Chem. 18 (1953), 1511–1515; JP-A-03223277—quoted in Chem. Abstracts 1992:128652 or 116:128652).

The amino compounds of the general formula (IV) are obtained when corresponding cyclic ketones (one of the radicals $A^1$, $A^2$ or $A^3$ then representing —CO—) are reacted with formamide at temperatures between 140° C. and 190° C., and the resulting formylamino compound is subsequently hydrolysed by heating with aqueous hydrochloric acid (cf J. Org. Chem. 18 (1953), 1511–1515), or when the corresponding cyclic ketones are initially, by reaction with hydroxylamine hydrochloride, if appropriate in the presence of a diluent, such as, for example, pyridine, at temperatures between 0° C. and 50° C., converted into corresponding oximes and these are then reacted with a reducing agent, such as, for example, sodium borohydride, in the presence of a reaction auxiliary, such as, for example, titanium (IV) chloride, and in the presence of a diluent, such as, for example, 1,2-dimethoxyethane, at temperatures between −20° C. and +50° C. (cf. the Preparation Examples).

The corresponding cyclic ketones are known and/or can be prepared by processes known per se (cf. J. Chem. Soc. 1953, 1837–1842; J. Heterocycl. Chem. 2 (1965), 44–48; loc. cit. 17 (1980), 87–92; loc. cit. 29 (1992), 1213–1217; J. Pharm. Sci. 52 (1963), 898–901; U.S. Pat No. 3,301,874).

The formula (III) provides a general definition of the alkoxycarbonyl compounds further to be used as starting materials in the process according to the invention for preparing compounds of the general formula (I). In the general formula (III), $R^3$ preferably or in particular has that meaning which has already been mentioned above, in connection with the description of the compounds of the general formula (I) according to the invention, as being preferred or as being particularly preferred for $R^3$; R' preferably represents alkyl having 1 to 4 carbon atoms, in particular methyl or ethyl.

The starting materials of the general formula (III) are known chemicals for synthesis.

The process according to the invention for preparing the compounds of the formula (I) is, if appropriate, carried out using a reaction auxiliary. Suitable reaction auxiliaries are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N,-dimethyl-cyclohexylamine, dicyclohexylamine, ethyl-dicyclohexylamine, N,N-dimethyl-aniline, N,N-di-methyl-benzylamine, pyridine, 2-methyl-, 3-methyl-, 4methyl-, 2,4-dimethyl-, 2,6-dimethyl-, 3,4dimethyl- and 3,5-dimethyl-pyridine, 5-ethyl-2-methyl-pyridine, 4di-methylamino-pyridine, N-methyl-piperidine, 1,4-diazabicyclo[2,2,2]-octane (DABCO), 1,5-diazabicyclo[4,3,0]-non-5-ene (DBN), or 1,8 diazabicyclo[5,4,0]-undec-7-ene (DBU).

The process according to the invention for preparing the compounds of the general formula (I) is, if appropriate, carried out using a diluent. Suitable diluents are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the process according to the invention, the reaction temperatures can be varied within a relatively wide range. In general, the process is carried out at temperatures between 0° C. and 150° C., preferably between 10° C. and 120° C.

The process according to the invention is generally carried out under atmospheric pressure. However, it is also possible to carry out the process according to the invention under elevated or reduced pressure—in general between 0.1 bar and 10 bar.

In carrying out the process according to the invention, the starting materials are generally employed in approximately equimolar amounts. However, it is also possible to employ a relatively large excess of one of the components. The reaction is generally carried out in a suitable diluent in the presence of a reaction auxiliary and the reaction mixture is generally stirred for a number of hours at the temperature required. Work-up is carried out by customary methods (cf. the Preparation Examples).

The active compounds according to the invention can be used as defoliants, desiccants, haulm killers and, especially, as weed-killers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindermia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicun, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera, Aegilops and Phalaris.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The active compounds according to the invention are suitable, depending on the concentration, for the total control of weeds, for example on industrial terrain and railway tracks, and on paths and squares with or without tree plantings. Equally, the active compounds according to the invention can be employed for the control of weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, in lawns, turf and pasture-land, and for the selective control of weeds in annual crops.

The compounds of the formula (I) according to the invention have strong herbicidal activity and a broad activity spectrum when used on the soil and on above-ground parts of plants. To a certain extent, they are also suitable for the selective control of monocotyledonous and dicotyledonous weeds in monocotyledonous and dicotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam formers.

If the extender used is water, it is also possible to employ, for example, organic solvents as auxiliary solvents. Suitable liquid solvents are essentially the following: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are for example crushed fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For the control of weeds, the active compounds according to the invention, as such or in their formulations, can also be used as mixtures with known herbicides, finished formulations or tank mixes being possible.

Possible components for the mixtures are known herbicides, for example acetochlor, acifluorfen(-sodium), aclonifen, alachor, alloxydim(-sodium), ametryne, amidochlor, amidosulfuron, anilofos, asulam, atrazine, azafenidin, azirmsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentraione(-ethyl), chlomethoxyfen, chloramben, chloridazon, chlorimuron(-ethyl), chlornitrofen, chlorsulfuron, chlorotoluron, cinidon(-ethyl), cinmethylin, cinosulfuron, clefoxydim, clethodim, clodinafop(-propargyl), clomazone, clomeprop, clopyralid, clopyrasulfuron(-methyl), cloransularn(-methyl), curnyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron (-methyl), ethofumesate, ethoxyfen, ethoxysulfuron(-methyl), etobenzanid, fenoxaprop(-P-ethyl), fentrazarnide, flamprop(-isopropyl), flamprop(-isopropyl-L), flamprop(-methyl), flazasulfuron, florasilam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-methyl), flurprimidol, flurtamone, fluthiacet(-methyl), fluthiamide, fomesafen, glufo-sinate(-ammonium), glyphosate(-isopropylammonium), halosafen, haloxy-fop(-ethoxyethyl), haloxyfop(-P-methyl), hexazinone, imazamethabenz-(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfltorfen, -paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac-(-methyl), pyrithiobac(-sodium), quinchlorac, quimnerac, quinoclamine, quizalofop (-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thia-fluamide, thiazopyr, thidiazimin, thifensulfuron(-methyl), thiobencarb, tiocarbazil, tralkoxydim, triallate, triasulfiron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

PREPARATION EXAMPLES

Example 1

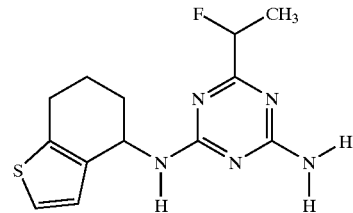

Process with Integrated Preparation of the Starting Material of the Formula (I)

A mixture of 3.5 g (18.4 mmol) of 4,5,6,7-tetrahydrobenzo[b]thiophen-4-yl-amine hydrochloride and 1.6 g (18.4 mmol) of cyanoguanidine is heated at 150° C. for two hours, then cooled in an acetone/dry ice bath and stirred with diethyl ether. The resulting crystalline solid is separated off by filtration and dissolved in 50 ml of methanol. The solution is admixed with 6.6 g (46.7 mmol) of sodium sulphate and, at room temperature (about 20° C.), 1.4 g (13.3 mmol) of methyl 2-fluoro-propanoate and 2.1 g (12.1 mmol) of sodium methoxide are then added successively. The reaction mixture is stirred at room temperature for 20 hours and subsequently concentrated under water-pump vacuum.

The residue is partitioned between water and dichloromethane and the organic phase is separated off, dried over sodium sulphate and filtered. The filtrate is concentrated under water-pump vacuum and the residue is purified by column chromatography (silica gel, ethyl acetate/hexane, vol.: 20:80)).

This gives 0.84 g (16% of theory) of 2-amino-4-(1-fluoroethyl)-6-(4,5,6,7-tetra-hydrobenzo[b]thiophen-4-yl-amino)-1,3,5-triazine as a pale yellow oil logP=4.26[a)]

Analogously to Example 1, and in accordance with the general description of the preparation process according to the invention, it is also possible to prepare, for example, the compounds of the general formula (I) listed in Table 1 below.

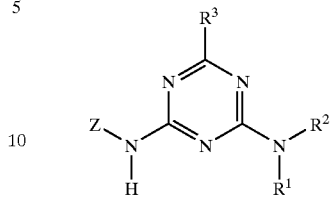

TABLE 1

Examples of the compounds of the formula (I)

| Ex. No. | $R^1$ | $R^2$ | $R^3$ | Z | Physical Data |
|---|---|---|---|---|---|
| 2 | — | NR¹NR²: \ N=CH−N(CH₃)₂ | CHFCH₃ | tetrahydrobenzo[b]thiophen-4-yl | |
| 3 | H | —CO—CH₃ | CHFCH₃ | tetrahydrobenzo[b]thiophen-4-yl | |
| 4 | H | —CO—C₂H₅ | CHFCH₃ | tetrahydrobenzo[b]thiophen-4-yl | |
| 5 | H | H | CF(CH₃)₂ | tetrahydrobenzo[b]thiophen-4-yl | logP = 1.75[a)] |
| 6 | — | NR¹NR²: \ N=CH−N(CH₃)₂ | CF(CH₃)₂ | tetrahydrobenzo[b]thiophen-4-yl | logP = 2.67[b)] |
| 7 | H | —CO—CH₃ | CF(CH₃)₂ | tetrahydrobenzo[b]thiophen-4-yl | logP = 2.66[a)] |
| 8 | H | —CO—C₂H₅ | CF(CH₃)₂ | tetrahydrobenzo[b]thiophen-4-yl | logP = 2.93[a)] |

TABLE 1-continued

Examples of the compounds of the formula (I)

| Ex. No. | R¹ | R² | R³ | Z | Physical Data |
|---|---|---|---|---|---|
| 9 | H | H | CHCl$_2$ | 4,5,6,7-tetrahydrobenzothiophen-4-yl | |
| 10 | H | H | CF$_2$Cl | 4,5,6,7-tetrahydrobenzothiophen-4-yl | logP = 3.01[a] |
| 11 | H | H | C$_2$F$_5$ | 4,5,6,7-tetrahydrobenzothiophen-4-yl | |
| 12 | H | H | CH$_2$OCH$_3$ | 4,5,6,7-tetrahydrobenzothiophen-4-yl | |
| 13 | H | H | n-C$_3$H$_7$ | 4,5,6,7-tetrahydrobenzothiophen-4-yl | logP = 1.61[a] |
| 14 | H | H | i-C$_3$H$_7$ | 4,5,6,7-tetrahydrobenzothiophen-4-yl | |
| 15 | H | H | CF$_3$ | 4,5,6,7-tetrahydrobenzothiophen-4-yl | |
| 16 | H | H | CF$_3$ | 2-methyl-4,5,6,7-tetrahydrobenzothiophen-4-yl | logP = 3.27[a] |
| 17 | H | H | CHFCH$_3$ | 2-methyl-4,5,6,7-tetrahydrobenzothiophen-4-yl | logP = 1.97[a] |

TABLE 1-continued

Examples of the compounds of the formula (I)

| Ex. No. | R¹ | R² | R³ | Z | Physical Data |
|---|---|---|---|---|---|
| 18 | H | H | CF(CH₃)₂ | (4-methyl-2-methyl-4,5,6,7-tetrahydrobenzothiophene) | logP = 2.03ᵃ⁾ |
| 19 | H | H | CF₃ | (2-chloro-4-methyl-4,5,6,7-tetrahydrobenzothiophene) | |
| 20 | H | H | CHFCH₃ | (2-chloro-4-methyl-4,5,6,7-tetrahydrobenzothiophene) | |
| 21 | H | H | CF(CH₃)₂ | (2-chloro-4-methyl-4,5,6,7-tetrahydrobenzothiophene) | |
| 22 | H | H | CF₃ | (7-methyl-4,5,6,7-tetrahydrobenzo[c]thiophene) | |
| 23 | H | H | CHFCH₃ | (7-methyl-4,5,6,7-tetrahydrobenzo[c]thiophene) | |
| 24 | H | H | CF(CH₃)₂ | (7-methyl-4,5,6,7-tetrahydrobenzo[c]thiophene) | |
| 25 | H | H | CF₃ | (1,3-dimethyl-7-methyl-4,5,6,7-tetrahydrobenzo[c]thiophene) | |

TABLE 1-continued
Examples of the compounds of the formula (I)
| Ex. No. | R¹ | R² | R³ | Z | Physical Data |
|---|---|---|---|---|---|
| 26 | H | H | CHFCH₃ | 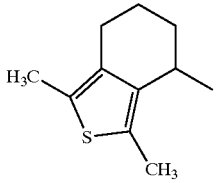 | logP = 2.21[a)] |
| 27 | H | H | CF(CH₃)₂ | 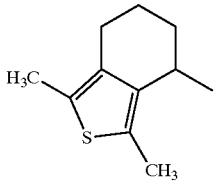 | |
| 28 | H | H | CF₃ | 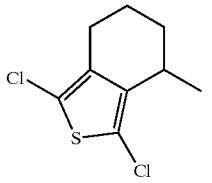 | |
| 29 | H | H | CHFCH₃ | 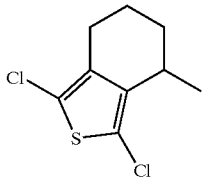 | |
| 30 | H | H | CF(CH₃)₂ | 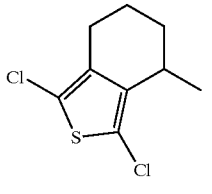 | |
| 31 | H | H | CF₃ | 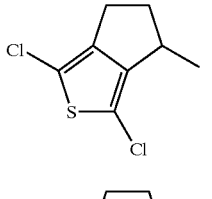 | |
| 32 | H | H | CHFCH₃ | 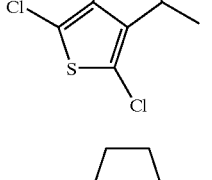 | |
| 33 | H | H | CF(CH₃)₂ | 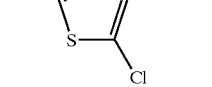 | |

TABLE 1-continued
Examples of the compounds of the formula (I)
| Ex. No. | R¹ | R² | R³ | Z | Physical Data |
|---|---|---|---|---|---|
| 34 | H | H | CF₃ | 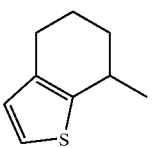 | |
| 35 | H | H | CHFCH₃ | 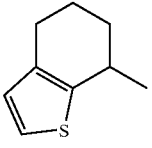 | |
| 36 | H | H | CF(CH₃)₂ | 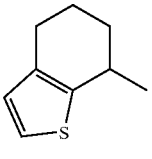 | |
| 37 | H | H | CF₃ | 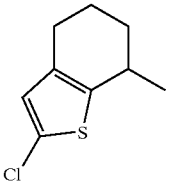 | |
| 38 | H | H | CHFCH₃ | 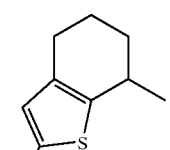 | |
| 39 | H | H | CF(CH₃)₂ | 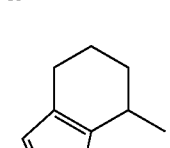 | |
| 40 | H | H | CF₃ | 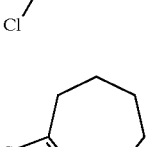 | |
| 41 | H | H | CHFCH₃ | 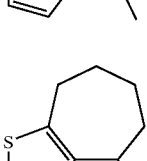 | |

TABLE 1-continued

Examples of the compounds of the formula (I)

| Ex. No. | R¹ | R² | R³ | Z | Physical Data |
|---|---|---|---|---|---|
| 42 | H | H | CF(CH$_3$)$_2$ | | |
| 43 | H | H | CF$_3$ | | logP = 3.47[a] |
| 44 | H | H | CHFCH$_3$ | | logP = 2.16[a] |
| 45 | H | H | CF(CH$_3$)$_2$ | | |
| 46 | H | H | CF$_3$ | | |
| 47 | H | H | CHFCH$_3$ | | |
| 48 | H | H | CF(CH$_3$)$_2$ | | |
| 49 | H | H | CF$_3$ | | |
| 50 | H | H | CHFCH$_3$ | | |
| 51 | H | H | CF(CH$_3$)$_2$ | | |

TABLE 1-continued

Examples of the compounds of the formula (I)

| Ex. No. | R¹ | R² | R³ | Z | Physical Data |
|---|---|---|---|---|---|
| 52 | H | H | $CF_3$ | | |
| 53 | H | H | $CHFCH_3$ | | |
| 54 | H | H | $CF(CH_3)_2$ | | |
| 55 | H | H | $CF_3$ | | |
| 56 | H | H | $CHFCH_3$ | | logP = 2.47[a] |
| 57 | H | H | $CF(CH_3)_2$ | | |
| 58 | H | H | $CF_3$ | | |
| 59 | H | H | $CHFCH_3$ | | |
| 60 | H | H | $CF(CH_3)_2$ | | |
| 61 | H | H | $CF_3$ | | |

TABLE 1-continued

Examples of the compounds of the formula (I)

| Ex. No. | R¹ | R² | R³ | Z | Physical Data |
|---|---|---|---|---|---|
| 62 | H | H | CHFCH₃ | | |
| 63 | H | H | CF(CH₃)₂ | | |
| 64 | H | H | CF₃ | | |
| 65 | H | H | CHFCH₃ | | |
| 66 | H | H | CF(CH₃)₂ | | |

The logP values given in Example 1 and in Table 1 were determined in accordance with EEC Directive 79/831 Annex V.A⁸ by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data are labelled in Table 1 with [a].

(b) Mobile phases for the determination in the neutral range: 0.01 molar aqueous phosphate buffer solution, acetonitrile; linear gradient from 10% acetonitrile to 90% acetonitrile—corresponding data are labelled in Table 1 with [b].

Calibration was carried out using unbranched alkan-2-ones (with from 3 to 16 carbon atoms) whose logP values are known (determination of the logP values by the retention times using linear interpolation between two successive alkanones).

The lambda max values were determined using the UV spectra from 200 nm to 400 nm in the maxima of the chromatographic signals.

Starting Materials of the Formula (II)

Example II-1

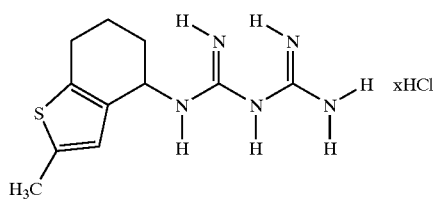

A mixture of 24.9 g (0.122 mol) of 2-methyl-4,5,6,7-tetrahydrobenzo[b]thiophen-4-yl-amine hydrochloride and 10.3 g (0.122 mol) of cyanoguanidine is heated at 150° C. for one hour and subsequently cooled in an acetone/dry ice bath. At −78° C., the reaction mixture is stirred with acetone and the resulting solid is filtered off, stirred at room temperature with diethyl ether and once again filtered.

This gives 27.3 g (78% of theory) of 2-methyl-4,5,6,7-tetrahydrobenzo[b]thiophen-4-yl-biguanide hydrochloride as a dark brown solid (logP=1.12 [a]).

Analogously to Example II-1, it is also possible to prepare, for example, the compounds of the general formula (II) listed in Table 2 below.

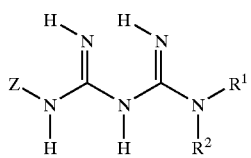

TABLE 2

Examples of the compounds of the formula (II) $R^1$ and $R^2$ in each case represent hydrogen

| Ex. No. | Z | Physical Data |
|---|---|---|
| II-2 | | LogP = 0.73[a.)] |
| II-3 | | |
| II-4 | | |
| II-5 | | |

Starting Materials of the Formula (IV):

Example IV-1

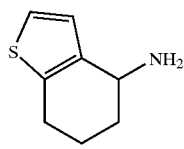

Step I

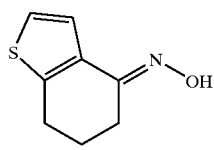

77.3 g (0.51 mol) of 6,7-dihydro-benzo[b]thiophen-4 (5H)-one together with 69.5 g (1.0 mol) of hydroxylamine hydrochloride are stirred in 600 ml of pyridine at room temperature (about 20° C.) for two hours. The reaction mixture is subsequently poured into 1 litre of water, a pH of 1 is adjusted using conc. hydrochloric acid and the mixture is extracted with ethyl acetate. The organic extract solution is dried over sodium sulphate and filtered. The filtrate is concentrated under water-pump vacuum and the residue which is obtained as a solid is stirred with petroleum ether and isolated by filtration with suction.

This gives 74.5 g (88% of theory) of 6,7-dihydro-benzo [b]thiophen-4(5H)-oxime as a 1:2 mixture of the E/Z isomers.

Step 2

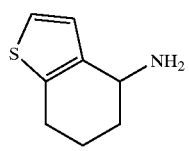

A solution of 8.4 g (50 mmol) of 6,7-dihydro-benzo[b] thiophen-4(5H)-oxime in 50 ml of 1,2-dimethoxy-ethane is added dropwise at 0° C. to a mixture of 20.0 g (105 mmol) of titanium(IV) chloride and 8.0 g (210 mmol) of sodium borohydride in 200 ml of 1,2-dimethoxy-ethane. The reaction mixture is kept in the ice/water bath and stirred for about 20 hours. For work-up, the mixture is poured into water and a pH of 9 is adjusted using 25% strength ammonia solution. The resulting precipitate is separated off by filtration through Cellite, and the filtrate is extracted with dichloromethane. The organic extract solution is dried over sodium sulphate and filtered. The filtrate is concentrated under water-pump vacuum.

This gives 4.5 g (59% of theory) of 4,5,6,7-tetra-hydro-benzo[b]thiophen4-yl-amine as a colourless oil.

The hydrochloride of the compound obtained according to Example IV-1 can be prepared, for example, as follows:

A mixture of 4.1 g (27 mmol) of 4,5,6,7-tetrahydro-benzo [b]thiophen-4yl-amine, 4 ml of conc. hydrochloric acid and 50 ml of methanol is stirred at room temperature (about 20° C.) for one hour and subsequently concentrated under water-pump vacuum. The residue is stirred with diethyl ether and the resulting crystalline product is isolated by filtration with suction.

This gives 3.8 g (75% of theory) of 4,5,6,7-tetrahydro-benzo[b]thiophen-4-yl-amine hydrochloride as a brown solid.

Use Examples

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 litre of water per hectare.

After three weeks, the degree of damage to the plants is rated in % damage in comparison to the development of the untreated control.

The figures denote:

0%=no effect (like untreated control)

100%=total destruction

In this test, for example, the compound according to Preparation Example 1 shows strong activity against weeds.

In this test, for example, the compound of Preparation Example 1 shows strong activity against weeds.

TABLE A

| Active compound according to Preparation Example No. | Application rate g of ai./ha | Alopecurus | Setaria | Abutilon | Amaranthus | Galium |
|---|---|---|---|---|---|---|
| 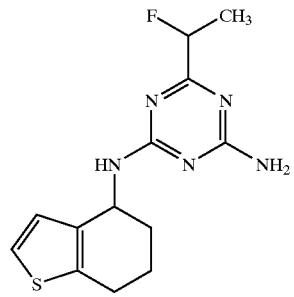 (1) | 500 | 100 | 100 | 95 | 100 | 90 |

Example B

Post-emergence Test
 Solvent: 5 parts by weight of acetone
 Emulsifier: 1 part by weight of alkylaryl polyglycol ether

TABLE B

| Active compound according to Preparation Example No. | Application rate g of ai./ha | Alopecurus | Setaria | Amaranthus | Sinapis | Xanthium |
|---|---|---|---|---|---|---|
| 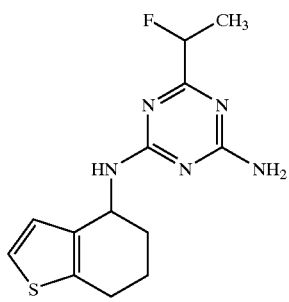 (1) | 500 | 95 | 100 | 100 | 100 | 100 |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:
 0%=no effect (like untreated control)
 100%=total destruction

What is claimed is:

1. A substituted triazine compound of the Formula (I)

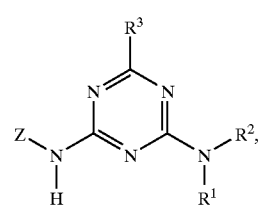

in which $R^1$ represents hydrogen or represents optionally substituted alkyl,

R² represents hydrogen, represents formyl or represents in each case optionally substituted alkyl, alkylcarbonyl, alkoxycarbonyl or alkylaminocarbonyl,
or the grouping N(R¹R²) also represents dialkylaminoalkylideneamino, R³ represents hydrogen, represents halogen, represents optionally substituted alkyl, represents in each case optionally substituted alkylcarbonyl, alkoxycarbonyl, alkoxy, alkylthio, alkylsulphinyl or alkylsulphonyl, represents in each case optionally substituted alkenyl or alkinyl, or represents optionally substituted cycloalkyl, and Z represents one of the thienocycloalk(en)yl groupings below

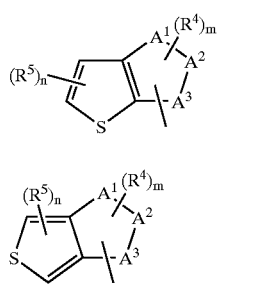

in which
m represents the numbers 0, 1, 2, 3 or 4,
n represents the numbers 0, 1 or 2,
$A^1$ represents O, S, —CO—, —CS— or alkanediyl,
$A^2$ represents O, S, —CO—, —CS— or alkanediyl,
$A^3$ represents O, S, —CO—, —CS— or alkanediyl,
with the proviso that at least one of the groupings $A^1$, $A^2$, $A^3$ represents alkanediyl and that two adjacent groups do not simultaneously represent S or O—

R⁴ represents amino, cyano, carbamoyl, thiocarbamoyl, formyl, halogen, or represents in each case optionally substituted alkyl, alkylcarbonyl, alkoxy, alkoxycarbonyl, alkylthio, alkylsulphinyl, alkylsulphonyl, alkylamino, dialkylamino, alkylcarbonylamino, alkoxycarbonylamino, alkylsulphonylamino, alkenyl, alkinyl, alkenylcarbonyl, alkinylcarbonyl, aryl, arylcarbonyl or arylalkyl, and R⁵ represents nitro, amino, cyano, carbamoyl, thiocarbamoyl, formyl, halogen, or represents in each case optionally substituted alkyl, alkylcarbonyl, alkoxy, alkoxycarbonyl, alkylthio, alkylsulphinyl, alkylsulphonyl, alkylamino, dialkylamino, alkylcarbonylamino, alkoxycarbonylamino, alkylsulphonylamino, alkenyl, alkinyl, alkenylcarbonyl, alkinylcarbonyl, aryl, arylcarbonyl or arylalkyl.

2. The compound according to claim 1, wherein
m represents the numbers 0, 1 or 2,
$A^1$ represents O, S, —CO—, —CS— or alkanediyl having 1 to 3 carbon atoms,
$A^2$ represents O, S, —CO—, —CS— or alkanediyl having 1 to 3 carbon atoms,
$A^3$ represents O, S, —CO—, —CS— or alkanediyl having 1 to 3 carbon atoms,
with the proviso that at least one of the groupings $A^1$, $A^2$, $A^3$ represents alkanediyl having 1 to 3 carbon atoms and that two adjacent groups do not simultaneously represent S or O—

R¹ represents hydrogen or represents optionally cyano-, halogen- or $C_1$–$C_4$-alkoxy-substituted alkyl having 1 to 6 carbon atoms, R² represents hydrogen, represents formyl or represents in each case optionally cyano-, halogen- or $C_1$–$C_4$-alkoxy-substituted alkyl, alkylcarbonyl, alkoxycarbonyl or alkylaminocarbonyl having in each case 1 to 6 carbon atoms in the alkyl groups, or the grouping N(R¹R²) represents dialkylaminoalkylideneamino having in each case up to 4 carbon atoms in the alkyl groups or alkylidene groups, R³ represents hydrogen, represents halogen, represents optionally cyano-, halogen-, hydroxyl-, $C_1$–$C_4$-alkoxy- or $C_1$–$C_4$-alkylthio-substituted alkyl having 1 to 6 carbon atoms, represents in each case optionally cyano-, halogen- or $C_1$–$C_4$-alkoxy-substituted alkylcarbonyl, alkoxycarbonyl, alkoxy, alkylthio, alkylsulphinyl or alkylsulphonyl having in each case 1 to 6 carbon atoms in the alkyl groups, represents in each case optionally halogen-substituted alkenyl or alkinyl having in each case 2 to 6 carbon atoms, or represents optionally cyano-, halogen- or $C_1$–$C_4$-alkyl-substituted cycloalkyl having 3 to 6 carbon atoms, R⁴ represents amino, cyano, carbamoyl, thiocarbamoyl, formyl, halogen, represents in each case optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, dialkylamino, alkylcarbonylamino, alkoxycarbonylamino or alkylsulphonylamino having in each case 1 to 6 carbon atoms in the alkyl groups, represents in each case optionally cyano- or halogen-substituted alkenyl, alkinyl, alkenylcarbonyl or alkinylcarbonyl having in each case 2 to 6 carbon atoms in the alkenyl or alkinyl groups, or represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy- or $C_1$–$C_4$-alkoxy-carbonyl-substituted aryl, arylcarbonyl or arylalkyl having in each case 6 or 10 carbon atoms in the aryl group and optionally 1 to 4 carbon atoms in the alkyl moiety, and R⁵ represents nitro, amino, cyano, carbamoyl, thiocarbamoyl, formyl, halogen, represents in each case optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, dialkylamino, alkylcarbonylamino, alkoxycarbonylamino or alkylsulphonylamino having in each case 1 to 6 carbon atoms in the alkyl groups, represents in each case optionally cyano- or halogen-substituted alkenyl, alkinyl, alkenylcarbonyl or alkinylcarbonyl having in each case 2 to 6 carbon atoms in the alkenyl or alkinyl groups, or represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy- or $C_1$–$C_4$-alkoxy-carbonyl substituted aryl, arylcarbonyl or arylalkyl having in each case 6 or 10 carbon atoms in the aryl group and optionally 1 to 4 carbon atoms in the alkyl moiety.

3. The compound according to claim 1 wherein
$A^1$ represents O, S, —CO—, —CS—, methylene, dimethylene or trimethylene,
$A^2$ represents O, S, —CO—, —CS—, methylene, dimethylene or trimethylene,
$A^3$ represents O, S, —CO—, —CS—, methylene, dimethylene or trimethylene, with the proviso that at least one of the groupings $A^1$, $A^2$, $A^3$ represents methylene, dimethylene or trimethylene and that two adjacent groups do not simultaneously represent S or O—

$R^1$ represents hydrogen or represents in each case optionally cyano-, fluorine-, chlorine-, methoxy- or ethoxy-substituted methyl, ethyl, n- or i-propyl, $R^2$ represents hydrogen, represents formyl or represents in each case optionally cyano-, fluorine-, chlorine-, methoxy- or ethoxy-substituted methyl, ethyl, n- or i-propyl, acetyl, propionyl, n- or i-butyroyl, methoxycarbonyl, ethoxycarbonyl, n- or i-propoxycarbonyl, methylamino-carbonyl, ethylaminocarbonyl, n- or i-propylaminocarbonyl, or the grouping $N(R^1R^2)$ represents dimethylaminomethyleneamino or diethylaminomethyleneamino, $R^3$ represents hydrogen, represents fluorine, chlorine, bromine, represents in each case optionally cyano-, fluorine-, chlorine-, bromine-, hydroxyl-, methoxy-, ethoxy-, n- or i-propoxy-, methylthio-, ethylthio-, n- or i-propylthio-substituted methyl, ethyl, n- or i-propyl, n-, i- or s-butyl, represents in each case optionally cyano-, fluorine-, chlorine-, methoxy- or ethoxy- substituted acetyl, propionyl, n- or i-butyroyl, methoxycarbonyl, ethoxycarbonyl, n- or i-propoxycarbonyl, methoxy, ethoxy, n- or i-propoxy, methylthio, ethylthio, n- or i-propyl-thio, methylsulphinyl, ethylsulphinyl, n- or i-propylsulphinyl, methylsulphonyl, ethylsulphonyl, n- or i-propylsulphonyl, represents in each case optionally fluorine-, chlorine- or bromine-substituted ethenyl, propenyl, butenyl, ethinyl, propinyl or butinyl, or represents in each case optionally cyano-, fluorine-, chlorine-, methyl- or ethyl-substituted cyclopropyl, cyclobutyl, cyclopentyl or cyclohexyl, $R^4$ represents amino, cyano, carbamoyl, thiocarbamoyl, formyl, fluorine, chlorine, bromine, represents in each case optionally cyano-, fluorine-, chlorine-, methoxy- or ethoxy-substituted methyl, ethyl, n- or i-propyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, dimethyl-amino, diethylamino, acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, represents in each case optionally cyano-, fluorine-, chlorine- or bromine-substituted ethenyl, propenyl, butenyl, ethinyl, propinyl, butinyl, ethenylcarbonyl;, propenylcarbonyl, butenyl-carbonyl, ethinylcarbonyl, propinylcarbonyl or butinylcarbonyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, benzoyl or benzyl, and $R^5$ represents nitro, amino, cyano, carbamoyl, thiocarbamoyl, formyl, fluorine, chlorine, bromine, represents in each case optionally cyano-, fluorine-, chlorine-, methoxy- or ethoxy-substituted methyl, ethyl, n- or i-propyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, dimethylamino, diethylamino, acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, represents in each case optionally cyano-, fluorine-, chlorine- or bromine-substituted ethenyl, propenyl, butenyl, ethinyl, propinyl, butinyl, ethenylcarbonyl, propenylcarbonyl, butenyl-carbonyl, ethinylcarbonyl, propinylcarbonyl or butinylcarbonyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, benzoyl or benzyl.

4. The compound according to claim 1 wherein $A^1$ represents methylene or dimethylene, $A^2$ represents methylene or dimethylene, $A^3$ represents methylene or dimethylene, $R^1$ represents hydrogen, $R^2$ represents hydrogen, represents formyl or represents in each case optionally fluorine-, chlorine-, methoxy- or ethoxy-substituted acetyl, propionyl, n- or i-butyroyl, methoxycarbonyl, ethoxycarbonyl, n- or i-propoxycarbonyl, or the grouping $N(R^1R^2)$ represents dimethylaminomethyleneamino, $R^3$ represents in each case optionally fluorine- or chlorine-substituted methyl, ethyl, n- or i-propyl, $R^4$ represents cyano, fluorine, chlorine, bromine, or represents in each case optionally fluorine- or chlorine-substituted methyl, ethyl, methoxy or ethoxy, and $R^5$ represents nitro, cyano, fluorine, chlorine, bromine, or represents in each case optionally fluorine- or chlorine-substituted methyl, ethyl, methoxy or ethoxy.

5. The compound according to claim 1 wherein z represents

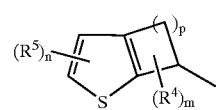

where p represents 2, 3 or 4, and n, m, $R^4$ and $R^5$ are as defined in claim 1.

6. A process for preparing the substituted triazine according to the Formula (I) of claim 1 wherein biguanides of the Formula (II)

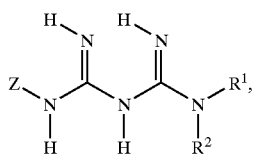
(II)

in which
R¹, R² and Z are as defined in claim 1, and/or acid adducts of compounds of the Formula (II) are reacted with alkoxycarbonyl compounds of the Formula (III)

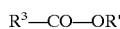
(III)

in which
R³ is as defined in claim 1 and
R¹ represents alkyl,
optionally in the presence of a reaction auxiliary and optionally in the presence of a diluent.

7. A compound of the Formula (II)

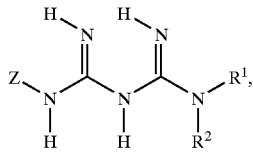
(II)

and acid adducts thereof, wherein
R¹, R² and Z are as defined in claim 1.

8. A process for preparing the compound of the Formula (II) according to claim 7, wherein an amino compound of the Formula (IV)

(IV)

in which
Z is as defined in claim 1,
and/or acid adducts of said compound of the Formula (IV) are reacted with a cyanoguanidine of the Formula (V)

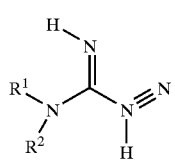
(V)

optionally in the presence of a reaction auxiliary and optionally in the presence of a diluent at temperatures between 100° C. and 200° C.

9. A method for controlling undesirable vegetation, comprising the step of allowing an effective amount of the compound according to claim 1 to act on said undesirable vegetation and/or its habitat.

10. An herbicidal composition comprising a compound according to claim 1 and a member selected from the group consisting of an extender, a surfactant, and combinations thereof.

* * * * *